United States Patent [19]

Schmidt

[11] 4,352,894

[45] Oct. 5, 1982

[54] STABLE AQUEOUS IMPREGNATING SOLUTIONS PREPARED FROM HYDROLYZED ALKYLTRIALKOXYSILANES

[75] Inventor: Werner Schmidt, St. Augustin, Fed. Rep. of Germany

[73] Assignee: Dynamit Nobel, Troisdorf, Fed. Rep. of Germany

[21] Appl. No.: 304,480

[22] Filed: Sep. 22, 1981

[30] Foreign Application Priority Data

Oct. 2, 1980 [DE] Fed. Rep. of Germany ....... 3037220

[51] Int. Cl.$^3$ ............................................... C08J 9/40
[52] U.S. Cl. ....................................... 521/91; 521/53; 521/141; 521/154; 521/918
[58] Field of Search ................... 521/91, 141, 918, 53, 521/154

[56] References Cited

U.S. PATENT DOCUMENTS 2,636,013 4/1953 Wilson et al. ........................ 521/141
2,737,398 6/1973 Yamaguchi ......................... 521/141

*Primary Examiner*—Morton Foelak
*Attorney, Agent, or Firm*—Felfe & Lynch

[57] ABSTRACT

This invention relates to solutions of silanols prepared by hydrolysis of alkyltrialkoxysilanes whose alkoxy groups are partially or completely hydrolyzed.

Preferred hydrolyzed alkyltrialkoxysilanes are of the formula $CH_3—CH_2—CH_2—Si(OH)_n(OH')_{3-n}$.

4 Claims, No Drawings

STABLE AQUEOUS IMPREGNATING SOLUTIONS PREPARED FROM HYDROLYZED ALKYLTRIALKOXYSILANES

This invention relates to solutions of silanols prepared by hydrolysis of alkyltrialkoxysilanes whose alkoxy groups are partially or completely hydrolyzed.

These solutions are stable for as long as several days, depending on the conditions of their preparation. They are particularly well suited for use as water repellents for inorganic-oxidic materials.

It is known that alkyltrialkoxysilanes can be used as impregnating agents for masonry, concrete or other inoranic oxidic materials, from German Pat. No. 20 29 446. While these alkyltrialkoxysilanes are liquids, they are employed as dilute solutions, the preferred solvents being alcohols. It has not been possible up to now to use solutions in water since alkyltrialkoxysilanes are but sparingly, if at all, soluble in water. Hydrolytic splitting of the ester groups usually also will not give a stable water-soluble product since under the conditions of hydrolysis the OH groups of the silanols formed are so reactive that they react quickly with other hydroxyl groups which may come either from the inorganic-oxidic materials or from vicinal silanols. Because of the possibilities for such reaction, aqueous solutions of alkyltrialkoxysilanes are not stable.

On the other hand, the reactivity of the OH groups of alkylsilanols results in rapid anchoring of the alkyltrialkoxysilanes on the inorganic-oxidic surface, with which the silanols formed as as intermediate during hydrolysis react to produce a strong bond between the alkylsilane and the surface to be impregnated. However, this reaction resulting in a strong bond can occur only after the hydrolysis of the alkyltrialkoxysilane has been completed.

Alcoholic solutions of alkyltrialkoxysilanes as impregnating agents further have the drawback that they are flammable. Especially when working in closed rooms, the evaporating alcohol can easily lead to a fire. The use of water as solvent in place of alcohol with a view to avoiding this drawback has not been possible because of the insolubility of alkyltrialkoxysilanes in water.

In the case of hydrolytic decomposition in an aqueous medium, however, such solutions are not stable, because of the reactivity of the silanols then forming, and quickly become turbid; and this instability of aqueous solutions of silanols is actually aggravated by the addition of basic media as required in many applications. (See U.S. Pat. No. 3,879,206.)

While aqueous solutions of alkyltrialkoxysilanes which are used as impregnating agents are known from German Pat. No. 10 69 057, these involve special silanes whose ester groups are glycol esters, which are difficult to hydrolyze and therefore will not form silanols with water without special additives. Thus no silanols are present in these solutions. Moreover, these special silanes do not act in the manner described above through the reaction of free hydroxyl groups with the surface but through the formation of a silicone resin that forms a film on the surface.

Thus there has been a need to develop an impregnating solution on the basis of alkyltrialkoxysilanes in which these silanes are present in hydrolyzed form and which is stable and contains no flammable solvent.

By way of filling this need, stable aqueous solutions of alkyltrialkoxysilanes have now been discovered in which the alkoxy groups are partially or completely substituted by hydroxyl groups. The alkyl groups of these silanols are straight-chain and may have up to 4 carbon atoms. The preferred alkyl group is the n-propyl group. The alkoxy groups of the alkyltrialkoxysilanes from which the present silanols are prepared have alkyl radicals with from 1 to 4 carbon atoms. The preferred silanols have the formula $CH_3-CH_2-CH_2-SI(OH)_n(OR')_{3-n}$, wherein $R'$ stands for an alkyl radical having from 1 to 4 carbon atoms and $n$ can assume values between 1 and 3.

Surprisingly, it has now been found that under specific conditions said trialkoxysilanes can be hydrolyzed to the corresponding water-soluble silanols, and that the aqueous solution which is so obtained is stable. While it is known that the mixing of alkyltrialkoxysilanes with acidulated water will yield the corresponding silanols, such solutions are unstable unless special measures are adopted. The silanols claimed, however, will be stable in aqueous solution if they are prepared at room temperature and the pH value of the solution is between 1.0 and 7.0, and preferably between 2.0 and 3.5.

The closer the pH value is to the neutral point in the preparation of these solutions, the longer the preparation of stable silanol solutions will take. It is therefore advisable to not exceed a pH of 5.0 in their preparation. The preferred pH range specified will result in preparation times that are acceptable in actual practice. The pH value is preferably adjusted by the use of strong mineral acids such as hydrochloric acid or sulfuric acid. However, strong organic acids such as formic acid are also suitable for this purpose.

In preparing these solutions, a mixture of alkyltrialkoxysilane and water is used without heating. The amount of water should be greater than the amount necessary for stoichiometric reaction. Advantageously, from 0.5 to 60 weight percent alkyltrialkoxysilane, based on the total solution, is used in preparing the solution. It is not necessary to heat this mixture since silanol formation is exothermic. However, the mixture may be heated slightly to accelerate the reaction; but temperatures above 40° C. should be avoided.

The alcohol liberated during hydrolysis will still be present in the silanol solution obtained. It is not necessary to eliminate it by distillation. The silanol solution may be diluted further with water, as required for a given application.

The concentration of the alkylsilanols in the solution may range from 0.5 to 45 weight percent. Preferably from 2 to 40 weight percent solutions are used.

For the purposes of the present invention, "stable" means that the silanols which are in solution will not spontaneously convert to higher-molecular-weight, water-insoluble siloxanes. In other words, depending on their acidity the solutions will remain free of turbidity for as long as 80 hours and longer, during which time they can effectively be used for impregnation. Such solutions standing for an extended period of time may further contain oligomerization products of the claimed silanes in solution.

It would have been reasonable to expect that water repellency could be imparted with the novel aqueous solutions of alkylsilanols to a given material as effectively as with an alcoholic solution of propyltrialkoxysilane. Surprisingly, however, it has been found that aqueous solutions of silanols are far better water repellents than alcoholic solutions of propyltrialkoxysilanes, for example. Thus, practically complete water repellency can be imparted to expanded chivadolimni or trachyte "glass", for example, both of which are siliceous materials used for insulating purposes, with a just 0.75% solution of silanol in water, whereas a 1% ethanolic solution of the corresponding alkylsilane will impart only about 40% water repellency. (See Example 2.) In the case of calcareous sandstone, the water-repelling effect of a 7.5% silanol solution is about equal to that of a 40% alcoholic propyltrialkoxysilane solution. (See Example 3.) Better water repellency is imparted also to porous clinker brick with a 1% aqueous silanol solution than with a 40% alcoholic propyltrialkoxysilane solution. (See Example 4.)

The materials to which water repellency is to be imparted generally are of an inorganic-oxidic and preferably siliceous nature, and they may also be foamed. These materials include synthetic or natural building materials such as calcareous sandstone, natural stone (sandstone, for example), trachyte, asbestos, asbestos cement, bloated or expanded clay, the various types of concrete, such as heavy concrete, light-weight concrete, aerated and foamed concretes, brick, roofing tile, mortar and plaster. These materials may be treated with the new impregnating solutions also on site to impart water repellency to them without the risk of solvent fires or toxic off-gases.

However, the water-repelling effect of aqueous silanol solutions is not limited to said oxide-silicate compounds. A high degree of water repellency can be imparted with the new alkylsilanol solutions also to foamed polyvinyl alcohol plastics. (See Example 6.)

EXAMPLE 1

Preparation of an aqueous silanol solution 50 g propyltrimethoxysilane is mixed with 50 g water to which 3 drops of 1% HCl has been added. With stirring at room temperature, the silane hydrolyzes within 10 to 15 minutes with mild evolution of heat, forming a clear solution of theoretically 37 g silantriol. The solution remains stable for at least three days before the onset of turbidity. It can be diluted with any desired amount of water to obtain the silane concentration required for a given end use.

If in place of propyltrimethoxysilane the corresponding ethoxy compound is used, the situation will be the same. The aqueous solution then theoretically contains 29 g silantriol.

EXAMPLE 2

Imparting water repellency to expanded chivadolimni 100 g each of the mineral chivadolimni of a particle size ranging from 0.5 to 2.5 mm and a specific gravity of 2400 kg/cm$^3$ were intimately mixed with 200 g each of the water-repellent solutions specified under (b) to (d) below and then dried for 2 hours at 120° C. The material so pretreated was then charged to a height of 24.6 cm into an upright tube with an inside diameter of 5 cm which had been closed at the bottom with a screen, and which was then weighed. The charge was held at the top by a plunger. Then the tube was immersed for 15 minutes above its filling level in water at room temperature, removed from the water, allowed to drip for 5 minutes while inclined 45 degrees, and weighed. The difference in the weight of the charged tube before and after immersion is a measure for the water repellency.

The uptake of water is expressed in weight percent, based on the dry weight of the mineral used.

TABLE 1

| | Treating agent | Uptake of water |
|---|---|---|
| (a) | Untreated | 265 |
| (b) | Ethanol | 236 |
| (c) | PTMO, 1 wt. % dissolved in ethanol | 168 |
| (d) | Propylsilanol, 1 wt. % dissolved in water | 71 |

PTMO = Propyltrimethoxysilane

As a blank test with water-saturated mineral showed, the amount of water mechanically adhering in the charged tube was in each case over 50% and must be deducted from all values given, so that practically complete water repellency was obtained with (d).

In the case of (c), the measurement was repeated after the silanized material had been stored for 16 days. The result was the same.

EXAMPLE 3

Impregnation of calcareous sandstone

A calcareous sandstone was dipped for 1 minute in the test solutions listed in Table 2, whereupon it was left to dry for 7 days at room temperature, weighed, and then stored hollow in water, in which it was immersed to a level 1 cm above its top surface. The amount of water taken up by the stone so stored was determined from time to time by weighing.

TABLE 2

| | Impregnating solution | Storage time in water | Uptake of water, percent |
|---|---|---|---|
| (a) | Water | 1 day | 11.5 |
| | | 5 days | 11.8 |
| | | 10 days | 12.2 |
| (b) | Aqueous hydrolyzate of 10% PTMO | 1 day | 0.3 |
| | | 5 days | 1.0 |
| | | 10 days | 1.0 |
| (c) | Alcoholic solution of 40% PTMO | 1 day | 0.4 |
| | | 5 days | 1.0 |
| | | 10 days | 1.1 |

PTMO = Propyltrimethoxysilane

It is apparent from this table that a silanol solution prepared with 10% PTMO has as good a water-repelling effect as a 40% alcoholic solution of the corresponding trimethoxysilane.

EXAMPLE 4

Imparting water repellency to clinker brick

Overburned porous clinker bricks were dipped as in Example 3 for 1 minute in the text solution specified in Table 3. After drying, they were weighed. The weighed bricks were immersed in water to a level 1 cm above their top surface. The uptake of water by the bricks so stored was determined from time to time by weighing.

TABLE 3

| | Impregnating solution | Storage time in water | Uptake of water, percent |
|---|---|---|---|
| (a) | Water | 1 day | 6.5 |
| | | 5 days | 7.2 |
| | | 10 days | 7.6 |
| (b) | Aqueous hydrolizate of 0.5% PTMO | 1 day | 1.3 |

TABLE 3-continued

| Impregnating solution | | Storage time in water | Uptake of water, percent |
|---|---|---|---|
| | | 5 days | 1.8 |
| | | 10 days | 2.0 |
| (c) | Aqueous hydrolyzate of 1.0% PTMO | 1 day | 0.6 |
| | | 5 days | 0.8 |
| | | 10 days | 1.0 |
| (d) | Ethanolic solution of 40% PTMO | 1 day | 0.2 |
| | | 5 days | 0.4 |
| | | 10 days | 1.4 |

PTMO = Propyltrimethoxysilane

Evaluated over a period of 10 days, an aqueous silanol solution of 1% PTMO is more effective than a 40% alcoholic silane solution.

EXAMPLE 5

Imparting water repellency to spheres of bloated clay

The bloated-clay spheres which are used as fillers for concrete have a diameter ranging from 4 to 8 mm and are porous and highly absorptive. To render them water-repellent, samples of such spheres were intimately mixed with an impregnating solution corresponding to 10% of the weight of the spheres. This amount of solution was absorbed completely by the spheres. The latter were then dried for 2 hours at 110° C. and after cooling stored in weighed lots under water. The uptake of water by the spheres was determined from time to time.

TABLE 4

| Impregnating solution | | Storage time in water | Uptake of water, percent |
|---|---|---|---|
| (a) | Water | 1 day | 18 |
| | | 3 days | 22 |
| | | 6 days | 27 |
| (b) | Aqueous hydrolyzate of 0.1% PTMO | 1 day | 4 |
| | | 3 days | 6 |
| | | 6 days | 11 |
| (c) | Aqueous hydrolyzate of 2.0% PTMO | 1 day | 3 |
| | | 3 days | 4 |
| | | 6 days | 8 |
| (d) | Aqueous hydrolyzate of 4.0% PTMO | 1 day | 1 |
| | | 3 days | 2 |
| | | 6 days | 4 |
| (e) | Ethanolic solution of 0.5% PTMO | 1 day | 4 |
| | | 3 days | 10 |
| | | 6 days | 15 |
| (f) | Ethanolic solution of 0.5% IBTMO | 1 day | 6 |
| | | 3 days | 12 |
| | | 6 days | 17 |
| (g) | Ethanolic solution of 4.0% IBTMO | 1 day | 6 |
| | | 3 days | 10 |
| | | 6 days | 13 |

PTMO = Propyltrimethoxysilane
IBTMO = Isobutyltrimethoxysilane

The percentages representing the active-substance content given in the table are based on the weight of the spheres.

It is apparent from the table that the effect of an aqueous silanol solution of 0.1% PTMO is not duplicated by solutions of silane in alcohol of from 5 to 40 times higher concentration.

EXAMPLE 6

Imparting water repellency to a foamed plastic

A sheet of foamed polyvinyl acetate plastic 5 mm thick was cut into strips measuring 5×17 cm. When such a strip, weighing about 14 g, was immersed for 15 minutes in cold water, it took up an amount of water corresponding to about 200% of its dry weight. This process was found to be reversible.

However, when the water contained a hydrolyzate of 2.5% PTMO, the process proved irreversible. After drying, the uptake of water by the foamed-plastic strip after 15 minutes' immersion then was only 15%, and after 30 minutes' immersion, 19%. A comparative test with an ethanolic solution of 2.5% isobutyltrimethoxysilane showed that after impregnation with the water repellent the uptake of water ranged from 80 to 93%.

It will be appreciated that the instant specification and examples are set forth by way of illustration and not of limitation, and that various changes and modifications may be made without departing from the spirit and scope of the present invention.

What is claimed is:

1. Method of impregnating a foamed polyvinyl alcohol plastic for the purpose of rendering it water repellent which comprises impregnating said foamed polyvinyl alcohol with a stable aqueous solution of hydrolyzed alkyltrialkoxysilane wherein the hydrolyzed alkyltrialkoxysilane has the formula $CH_3-CH_2-Si(OH)_n(OR')_{3-n}$ wherein R' stands for an alkyl radical having from 1 to 4 carbon atoms and n can assume values between 1 and 3.

2. Method of impregnating a foamed polyvinyl alcohol plastic for the purpose of rendering it water repellent which comprises impregnating said foamed polyvinyl alcohol with a stable aqueous solution as claimed in claim 1 wherein said hydrolized alkyltrialkoxysilane constitutes from 0.5 to 45 weight percent of the solution.

3. Method of impregnating a foamed polyvinyl alcohol plastic for the purpose of rendering it water repellent which comprises impregnating said foamed polyvinyl alcohol with a stable aqueous solution as claimed in claim 1 wherein said hydrolized alkyltrialkoxysilane constitute from 2 to 40 weight percent of the solution.

4. Method of impregnating a foamed polyvinyl alcohol plastic for the purpose of rendering it water repellent which comprises impregnating said foamed polyvinyl alcohol with a stable aqueous solution as claimed in claim 1 wherein the solution has a pH value of from 2–7.

* * * * *